United States Patent
Lechado et al.

(10) Patent No.: US 9,271,947 B2
(45) Date of Patent: Mar. 1, 2016

(54) USE OF PROPYL PROPANE THIOSULFINATE AND PROPYL PROPANE THIOSULFONATE FOR THE PREVENTION AND REDUCTION OF PARASITES IN AQUATIC ANIMALS

(71) Applicant: Investfood, LLC, Granada (ES)

(72) Inventors: Cristina Núñez Lechado, Granada (ES); Alberto Baños Arjona, Granada (ES); Enrique Guillamón Ayala, Granada (ES); Adela Valero López, Granada (ES); Mª Concepción Navarro Moll, Granada (ES); Ana Sanz Rus, Granada (ES)

(73) Assignee: Investfood, LLC, Granada (ES)

( * ) Notice: Subject to any disclaimer, the term of this patent is extended or adjusted under 35 U.S.C. 154(b) by 0 days.

(21) Appl. No.: 14/043,160

(22) Filed: Oct. 1, 2013

(65) Prior Publication Data
US 2015/0094381 A1    Apr. 2, 2015

(51) Int. Cl.
*A61K 31/105* (2006.01)
*A61K 31/10* (2006.01)
(Continued)

(52) U.S. Cl.
CPC ............... *A61K 31/10* (2013.01); *A01N 41/10* (2013.01); *A23K 1/1646* (2013.01); *A23K 1/188* (2013.01); *A61K 31/255* (2013.01)

(58) Field of Classification Search
None
See application file for complete search history.

(56) References Cited

U.S. PATENT DOCUMENTS 6,054,454 A    4/2000  Schmid et al.
6,486,128 B1 *  11/2002  Huq et al. ................. 514/30
(Continued)

FOREIGN PATENT DOCUMENTS

EP    1721534    11/2006
EP    2110128    10/2009
(Continued)

OTHER PUBLICATIONS

Tada Nasahiro, et al, "Nematicidal and antimicrobial constituents from Allium grayi Regel and Allium fistulosum L. var. caespitosum." Agricultural and Biological Chemistry, Japan Soc. for Bioscience, Biotechnology and Agrochem, vol. 52, No. 9, Jan. 1, 1988, pp. 2383-2385.
(Continued)

*Primary Examiner* — Marcos Szaidman
*Assistant Examiner* — Rayna B Rodriguez
(74) *Attorney, Agent, or Firm* — Steven M. Greenberg, Esq.; Kara A. Brotman, Esq.; CRGO Law

(57) ABSTRACT

A method for reducing parasites in aquatic animals is provided. The method includes reducing a plurality of parasites infecting an aquatic animal by administrating to the aquatic animal a compound comprising propyl propane thiosulfonate (PTSO) having the formula R—SOa-S—R, where R represents n-propyl group ($-CH_2-CH_2-CH_3$) and a is 2. In yet a different embodiment, a method for reducing a plurality of parasites infecting an aquatic animal includes administrating to the aquatic animal a compound comprising and propyl propane thiosulfinate (PTS) having the formula R—SOa-S—R, where R represents n-propyl group ($-CH_2-CH_2-CH_3$) and a is 1. In even yet another embodiment, a method for preventing a plurality of parasites in aquatic animals is provided and includes administrating to an aquatic animal a compound including PTS. In a different embodiment, a method for preventing a plurality of parasites in aquatic animals is provided and includes administrating to an aquatic animal a compound including PTSO.

7 Claims, 6 Drawing Sheets

(51) Int. Cl.
*A01N 41/10* (2006.01)
*A23K 1/18* (2006.01)
*A23K 1/16* (2006.01)
*A61K 31/255* (2006.01)

(56) References Cited

U.S. PATENT DOCUMENTS

| | | |
|---|---|---|
| 2003/0055011 A1 | 3/2003 | Huq et al. |
| 2006/0122266 A1 | 6/2006 | Sinnis et al. |
| 2009/0018194 A1 | 1/2009 | Garcia-Pareja et al. |
| 2010/0035984 A1 | 2/2010 | Garcia Pareja et al. |
| 2013/0079402 A1 | 3/2013 | Bravo |

FOREIGN PATENT DOCUMENTS

| | | |
|---|---|---|
| MX | 2012011304 | 1/2013 |
| WO | WO9963824 | 12/1999 |
| WO | WO0162090 | 8/2001 |
| WO | WO2004084645 | 10/2004 |
| WO | WO2011120182 | 10/2011 |

OTHER PUBLICATIONS

Thilo Waag, et al, "Allicin and derivates are cysteine protease inhibitors with antiparasitic activity." Bioorganic & Medicinal Chemistry Letters, vol. 20, No. 18, Sep. 15, 2010, pp. 5541-5543.

Coralie O M Millet, et al, "Effect of garlic and allium-derived products on the growth and metabolism of Spironucleus vortens." Experimental Parasitology, vol. 127, No. 2, Feb. 1, 2011, pp. 490-499.

Kim Duk Kyung et al: "Improved resistance to Eimeria acervulina infection in chickens due to dietary supplementation with gardlic metabolites", BIOSIS, Jan. 14, 2013. (Abstract Only).

\* cited by examiner

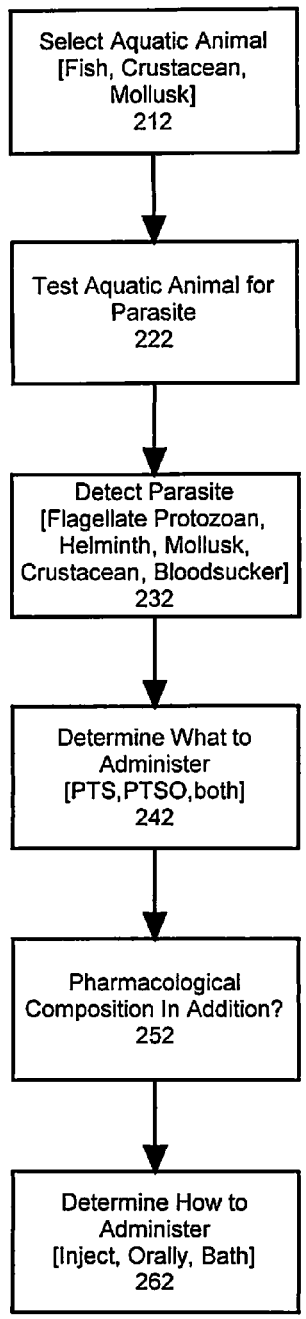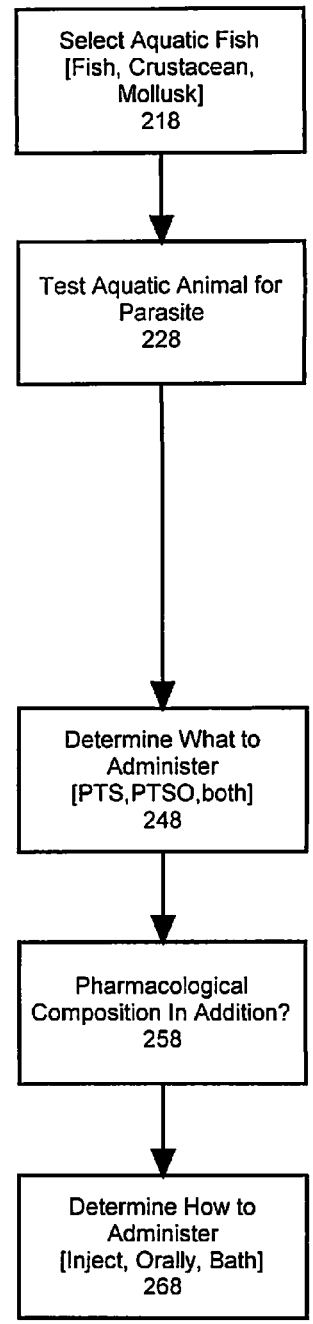
FIG. 2A   FIG. 2B

USE OF PROPYL PROPANE THIOSULFINATE AND PROPYL PROPANE THIOSULFONATE FOR THE PREVENTION AND REDUCTION OF PARASITES IN AQUATIC ANIMALS

BACKGROUND OF THE INVENTION

1. Field of the Invention

The present invention relates to aquaculture and, more particularly, to the prevention and reduction of parasites in aquatic animals.

2. Description of the Related Art

Aquaculture, also known as fish or shellfish farming, refers to the breeding, rearing, and harvesting of plants and animals in all types of water environments, including ponds, rivers, lakes, and oceans. Issues associated with aquaculture can include the propagation of invasive species, waste handling, side-effects of antibiotics, and competition between farmed and wild animals. In addition, the welfare of the animals in aquaculture can be impacted by stocking densities, behavioral interactions, diseases, and parasitosis.

Fish may be infected with numerous parasites belonging to various zoological groups. The most common types of infestation are caused by protozoans, like dinoflagellates ectoparasites, ciliates, and zooflagellates. Another species of interest in aquaculture is represented by helminth parasites, such as monogeneans, trematodes, cestodes and nematodes. In addition, parasites affecting aquaculture also include ectoparasites, such as mollusks, crustaceans, and sea lice.

The conventional strategies for controlling parasites and the resulting infections are expensive since they are based on chemoprophylaxis. Furthermore, the hardening of the regulations and the banning of the use of certain drugs, such as malachite green and gentian violet, against parasites in farms requires new approaches and strategies for parasite disease control.

BRIEF SUMMARY OF THE INVENTION

Embodiments of the present invention address deficiencies of the art in respect to the prevention and reduction of parasites in aquatic animals and provide a novel and non-obvious method for reducing parasites in aquatic animals. In an embodiment of the invention, propyl propane thiosulfinate (PTS) having the formula R—SOa-S—R, where R represents n-propyl group (—$CH_2$—$CH_2$—$CH_3$) and a is 1, can be administered to aquatic animals including fish, crustaceans, and molluscs, to reduce multiple, different parasites in the aquatic animals. Further, the concentration of PTS can be between at least one and no more than five thousand parts per million (1-5000 ppm).

In a different embodiment of the invention, propyl propane thiosulfonate (PTSO) having the formula R—SOa-S—R, where R represents n-propyl group (—$CH_2$—$CH_2$—$CH_3$) and a is 2, can be administered to an aquatic animal to reduce multiple, different parasites in the aquatic animal. Further, the concentration of PTSO can be between at least one and no more than five thousand parts per million (1-5000 ppm).

In yet a different embodiment of the invention, a compound including both propyl propane thiosulfonate (PTSO) having a formula R—SOa-S—R, where R represents n-propyl group (—$CH_2$—$CH_2$—$CH_3$) and a is 2, and also propyl propane thiosulfinate (PTS) having a formula R—SOa-S—R, where R represents n-propyl group (—$CH_2$—$CH_2$—$CH_3$) and a is 1, can be administered to a aquatic animal to reduce multiple, different parasites in the aquatic animal.

In even yet a different embodiment of the invention, a compound including both propyl propane thiosulfonate (PTSO) having a formula R—SOa-S—R, where R represents n-propyl group (—$CH_2$—$CH_2$—$CH_3$) and a is 2, and also propyl propane thiosulfinate (PTS) having a formula R—SOa-S—R, where R represents n-propyl group (—$CH_2$—$CH_2$—$CH_3$) and a is 1, can be administered to a fish to prevent multiple, different parasites from infecting the aquatic animal. In yet a different embodiment of the invention, PTS can be administered to an aquatic animal to prevent multiple, different parasites from infecting the aquatic animal. In another embodiment, PTSO can be administered to an aquatic animal to prevent multiple, different parasites from infecting the aquatic animal.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred; it being understood, however, that the invention is not limited to the precise arrangements and instrumentalities shown, wherein:

FIG. 2A is a flow chart illustrating a method for reducing parasites in aquatic animals;

FIG. 2B is a flow chart illustrating a method for preventing parasites in aquatic animals;

DETAILED DESCRIPTION OF THE INVENTION

Embodiments of the invention provide for combating parasites in aquatic animals, including fish, mollusks, and crustaceans. Specifically, propyl propane thiosulfonate (PTSO) and propyl propane thiosulfinate (PTS) can be used alone or in combination with each other as an anti-parasitic against a variety of parasites, such as flagellate protozoan, helminths, mollusks, crustaceans, and bloodsuckers, in aquatic animals, such as fish, mollusks, and crustaceans, so that parasites invading fish, mollusk, and crustaceans can both be reduced as well as prevented.

Figure 1:
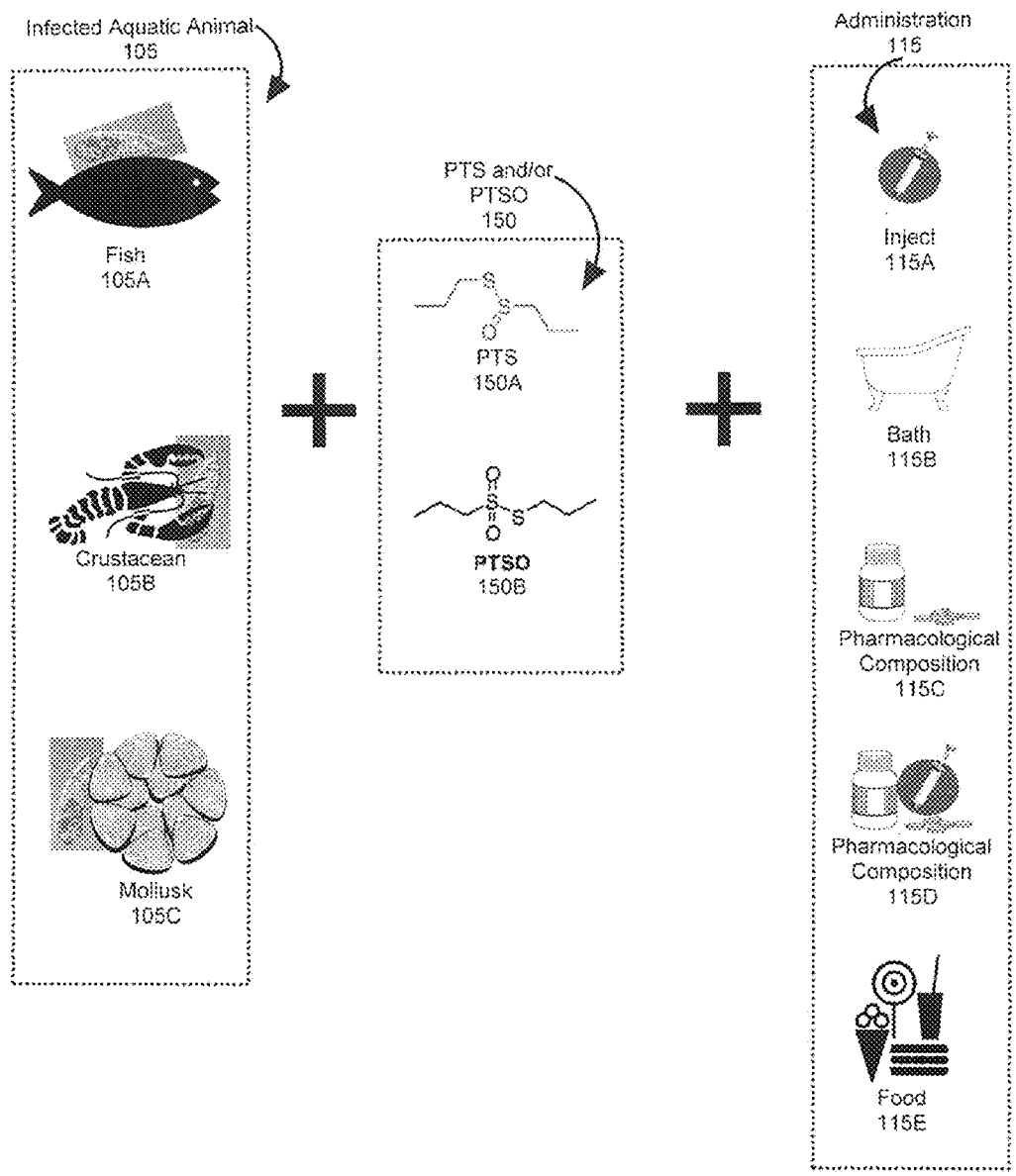
FIG. 1 is a pictorial illustration of a method for reducing parasites in aquatic animals.

In further illustration of the invention, FIG. 1 pictorially shows a process for reducing parasites in aquatic animals. Of note, in addition to reducing parasites in aquatic animals, it is contemplated that the invention can also be used to eliminate parasites in aquatic animals. Upon the detection of a plurality of parasites on and/or in infected aquatic animals 105, such as in and/or on fish 805A, crustaceans 805B, and mollusks 805C, propyl propane thiosulfonate (PTSO) 150B as well as propyl propane thiosulfinate (PTS) 150A can be used alone or in combination with each other 150 to reduce the number of parasites in or/and on the aquatic animals 105.

More specifically, upon the detection of a parasite, PTS and/or PTSO 150 can be administered 115 to an infected aquatic animal 105. The administration of PTS and/or PTSO 150 to an infected aquatic animal 105 can be accomplished via an injection 115A, a bath treatment 115B, incorporation with a pharmacological composition and orally administered 115C, incorporation with a pharmacological composition and injected 115D, or incorporated with food and then orally administrated 115E. In this way, after the administration of PTS and/or PTSO 150, the parasites in and/or on the infected aquatic animal 105 are reduced (and/or eliminated).

In yet further illustration of the invention, FIG. 2A is a flow chart illustrating a process for reducing parasites in aquatic animals. Beginning in block 212, an aquatic animal can be selected. The aquatic animal can be a fish (a member of a paraphyltic group of organisms that includes gill-bearing aquatic craniate animals), a crustacean, or a mollusk. The selected aquatic animal can be tested for the presence of parasites whether on and/or in the selected aquatic animal, as shown in block 222, by any method now known or later developed. Of note, testing can also include the visual inspection of the aquatic animal. As illustrated in block 232, upon the detection of a parasite, such as endoparasites and ectoparasites, including, but not limited to, flagellated protozoan, helminth, nematodes, trematodes, cestodes, bloodsuckers, copepods (such as sea lice), crustaceans, and mollusks, a determination as to what to administer to the infected aquatic animal can be made, as indicated in block 242.

Specifically, a determination can be made as to whether PTS, PTSO, or a combination of both should be administered. In addition, as shown in block 252, an optional determination as whether PTS, PTSO, or both can be administered in conjunction with a pharmacological composition, such as drugs and other anti-parasitic products, can be made. Further, a determination can be made as to how to administer PTS, PTSO, or both, as shown in block 262. For instance, administration of PTS, PTSO, or both can be accomplished via an injection, a bath treatment, or incorporated with food and then orally administrated in the aquatic animal. Further, if a pharmacological composition is also selected to be added, then PTS, PTSO, or both can be incorporated with the pharmacological composition and orally administered or incorporated with the pharmacological composition and injected.

In yet further illustration of the invention, FIG. 2B is a flow chart illustrating a process for preventing parasites in aquatic animals. As illustrated in FIG. 2B, an aquatic animal can be selected, as shown in block 218. As before, the aquatic animal can be a fish (a member of a paraphyltic group of organisms that includes gill-bearing aquatic craniate animals), a crustacean, or a mollusk. Optionally, an aquatic animal can be tested, by any method now known or later developed, including by visual inspection, to determining whether the selected aquatic animal is infected by a parasite (or multiple, different parasites), as illustrated in block 228. Regardless of whether it is determined that the selected aquatic animal is infected by parasites, as shown in block 248, a determination can be made as to what to administer to the selected aquatic animal—PTS, PTSO, both. In addition, as shown in block 258, an optional determination as whether PTS, PTSO, or both can be administered in conjunction with a pharmacological composition, such as drugs and other anti-parasitic products, can be made.

Also, a determination can be made as to how to administer PTS, PTSO, or both, as shown in block 268. For instance, administration of PTS, PTSO, or both can be accomplished via an injection, a bath treatment, or incorporated with food and then orally administered to the aquatic animal. Even yet further, if a pharmacological composition is also selected to be added, then PTS, PTSO, or both can be incorporated with the pharmacological composition and orally administered or incorporated with the pharmacological composition and injected. In this way, PTS, PTSO, or both, can be used in the prevention of parasites in aquatic animals.

Of note, as indicated herein the use of propyl propane thiosulfonate (PTSO) as well as propyl propane thiosulfinate (PTS) can be used alone or in combination with each other. In other words, PTS and PTSO can be used alone or in combination with each other in any relative percentage (in any ratio). In addition, PTS and PTSO can be used in combination with other anti-parasitic methods and products, including natural products or synthetic drugs, where PTS and/or PTSO can be in any ratio. The parasites can include endoparasites and ectoparasites, including, but are not limited to, flagellated protozoan, helminth, nematodes, trematodes, cestodes, bloodsuckers, copepods (such as sea lice), crustaceans, and mollusks. The aquatic animals being treated by PTS and/or PTSO can include, but are not limited to, fish (including fresh water and saline (marine) water species) such as salmon, trout, bass, seabream, fishbase, tilapia, turbot, cod, carp, sturgeon, flatfish, eel, tuna, catfish, coho, lobster, crab, mussel, clam, shrimp and prawn, mullet, shell, and oyster.

PTS and PTSO each correspond to the following formula:

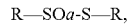

R—SO$_a$-S—R, in which R represents n-propyl group (—CH$_2$—CH$_2$—CH$_3$), and a is 1 for PTS and 2 for PTSO. Of note, PTSO is also known as dipropyl thiosulfonate (CAS Number 1113-13-9) and PTS is also known as dipropyl thiosulfinate (CAS Number 1948-52-3). The concentration of PTS used in an embodiment of the invention to reduce a plurality of parasites in and/or on a fish (and also in crustaceans and mollusks) can be between one and five thousand parts per million (1-5000 ppm). In a different embodiment, the concentration of PTS can be between five and one thousand parts per million (5-1000 ppm). In yet a different embodiment, the concentration of PTS can be between ten and three hundred fifty parts per million (10-350 ppm).

In yet even a different embodiment, the concentration of PTS can be between 10 and four hundred parts per million (10-400 ppm). The concentration of PTSO used in an embodiment of the invention to reduce a plurality of parasites in fish (as well as on fish) can be between one and five thousand parts per million (1-5000 ppm). In a different embodiment, the concentration of PTSO compound can be between five and one thousand parts per million (5-1000 ppm). In yet a different embodiment, the concentration of PTSO can be between ten and three hundred fifty parts per million (10-350 ppm). In yet even a different embodiment, the concentration of PTSO can be between 10 and four hundred parts per million (10-400 ppm).

In addition, PTS and/or PTSO can be administered to a healthy aquatic animal or an infected aquatic animal by an immersion treatment, such as a bath. In other words, PTS and/or PTSO can be used to reduce the number of parasites in and/or on an aquatic animal as well as PTS and/or PTSO can be used in the prevention of parasites in aquatic animals. In addition, PTS and/or PTSO can be incorporated into feed; the feed can then be administered to either a healthy aquatic animal or an infected aquatic animal. To that end, in a different embodiment, PTS and/or PTSO can be administered orally. For example, PTS and/or PTSO can be incorporated into a pharmacological composition (including drugs and other anti-parasitic products) and then the pharmacological composition can be orally administered to the aquatic animal.

In another embodiment, PTS and/or PTSO can be incorporated into a pharmacological composition (including drugs and other anti-parasitic products) and then the pharmacological composition can be injected into the aquatic animal. In addition, PTS and/or PTSO can be administered to an aquatic animal directly by injection alone (with just PTS, just PTSO, or only a mixture of PTS and PTSO).

In further illustration of the invention, the following examples are presented. Of note, as will be understood by one skilled in the art, the invention is not limited to just these examples.

Example 1

The parasiticide efficacy of a mixture of propyl propane thiosulfinate (PTS) and propyl propane thiosulfonate (PTSO) was measured in vitro against *Caligus rogercresseyi*.

Upon receipt in the laboratory, the wild adult females and males were kept in filtered seawater (125 μm membranes) in absolute darkness inside a thermo-regulated chamber at 12° C. The egg sacs were removed gently from females using a fine-tipped forceps and placed in separate beakers with 500 mL of filtered seawater in the conditions described above until spawning. The fish were then separated into the different stages: Nauplius I, Nauplius II, Copepodite and Adult for subsequent in vitro susceptibility studies.

In order to evaluate effectiveness, several bioassays were performed in triplicate with different concentrations of propyl propane thiosulfinate (PTS) and propyl propane thiosulfonate (PTSO) at each stage: Nauplio I, Nauplio II, Copepodite and Adult. In total, 40 *Caligus* were used per test and placed at a rate of 10 individuals per sterile petri plate. A mixture of propyl propane thiosulfinate (PTS) and propyl propane thiosulfonate (PTSO) at concentrations of 100, 200 and 300 ppm was added to each plate over a 30-minute exposure period. After that, the water was changed and the fish were incubated at 12° C. during a 12-hour photoperiod. A control group was also included. In order to estimate the effective lethal concentration and the survival ratio, observations were registered after treatment using the Kaplan-Meir function for each of the stages and treatments studied.

Example 2

In this example, a study of oral treatments of Ichthyobodosis in rainbow trout with different concentrations of Propyl propane thiosulphonate (PTSO) administered into feed was conducted.

Rainbow trout *Oncornynchus mykiss* were obtained from a local fish farm and acclimatized for at least 10 days before assay in 100l tanks with aeration in closed systems of water (15±2° C., pH 7-7.5). The natural light-dark cycle was simulated (12 h light: 12 h dark). Fish were fed twice per day with a commercial feed (EFICO, Biomar, Spain). Parasite-free fish were experimentally infested by holding the parasite-free fish 25 days in a 100 l tank that also contained fish showing high-intensity infestation (20 uninfected fish to 10 infected fish). Twenty (20) fish were then sampled at random for determination of infestation intensity, which was determined to be a high intensity infestation in at least 50% of fish.

Fish were anaesthetized by immersion in bath with 100 ppm of Tricaine methanesulfonate until respiration became weak. A mucus sample was then taken by gently scraping the body surface after examination of a sample area of 24×32 mm. The sample was mixed with 30 μl of distilled water on a slide, cover-slipped and examined to optic microscopy (400×).

Each treatment was assayed in 20 infected fish maintained in 100 L tanks with aeration in closed systems of water. The fish received feed containing three different treatments. The first group received a diet with 100 ppm of Propyl propane thiosulphonate (PTSO), the second received a diet supplemented with 300 ppm of PTSO, and the third received a diet with 300 ppm of metronidazole. All treatments were applied during a 10 day period. In all cases, feed was supplied at 2% of total body weight per day. Simultaneously, a positive control assay (also on 20 infected fish treated identically, but without any PTSO) and negative control assay (with 20 uninfected animals) were performed. Tanks conditions were identical to those during the acclimatization period. Throughout the assay period the fish were monitored regularly to ensure that the fish were eating the food, and to check for signs of toxicity.

Example 3

The objective of example 3 was to examine the activity of propyl propane thiosulphonate (PTSO) and propyl propane thiosulfinate (PTS) against L3 larvae of type I *Anisakis* and *Hysterotylacium aduncum* to explore the possible use of these compounds for prophylaxis treatments.

L3 of *Anisakis* type I and *Hysterotylacium aduncum* were collected by dissecting the fish *Micromesistius poutassou* (blue whiting) and *Trachurus trachurus* (mackerel) fished in the Cantabric sea, and selecting only larvae with a length greater than (>) 2.0 cm in the case of *Anisakis*, and greater than 0.8 cm for *Hysterotylacium*.

Larvae were axenised in antibiotic solution (Iglesias et al., 1997), introduced into polystyrene plate wells with 2 ml of sterile solution of 0.9% NaCl and the different concentrations of PTS alone, PTSO alone, and both PTS and PTSO (75, 200, 300 and 500 ppm) and then incubated at 36° C. in a 5% $CO_2$ atmosphere. As controls, larvae were assayed without test compound under identical experimental conditions, and using only the solvent DMSO 1% (Dimethyl sulfoxide). Larvae were examined under stereoscopic microscope at 4, 8, 24, and 48 hours to test the biocidal effect of the compounds. Larvae with no mobility at all were considered dead. Each dilution was tested three times on larvae from fish captured on different days.

Exemplary Results

The administration of PTS and PTSO demonstrated antiparasitic activity against stages of the life *C. rogercresseyi*.

Figure 3:
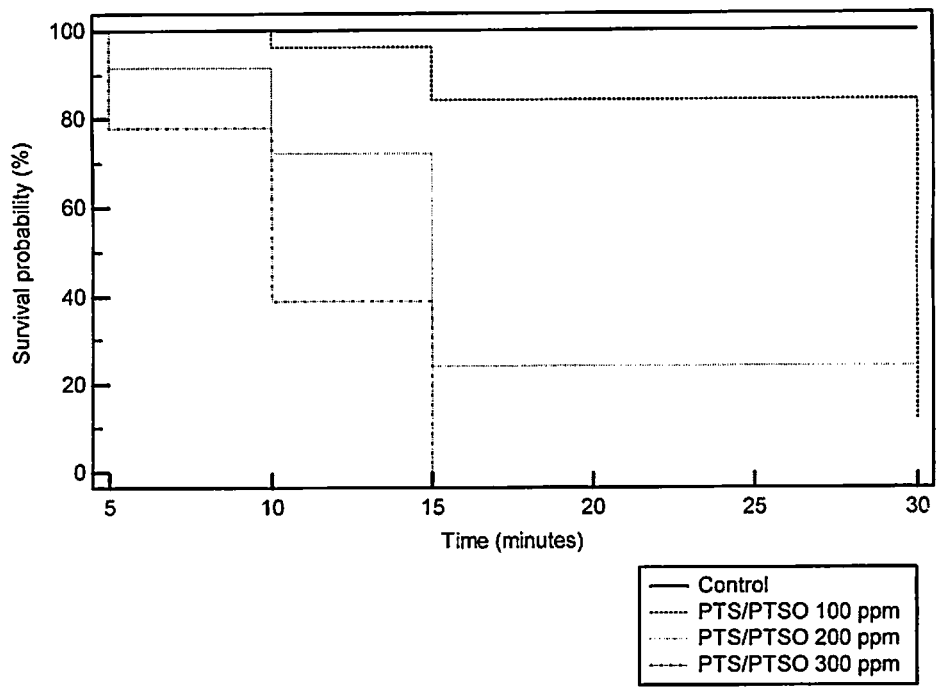
FIG. 3 illustrates the survival probability of *Caligus rogercresseyi* copepodites at different concentrations of PTS and PTSO.

For example, FIG. 3 illustrates the survival probability of *Caligus rogercresseyi* copepodites at different concentrations of PTS and PTSO.

Figure 4:
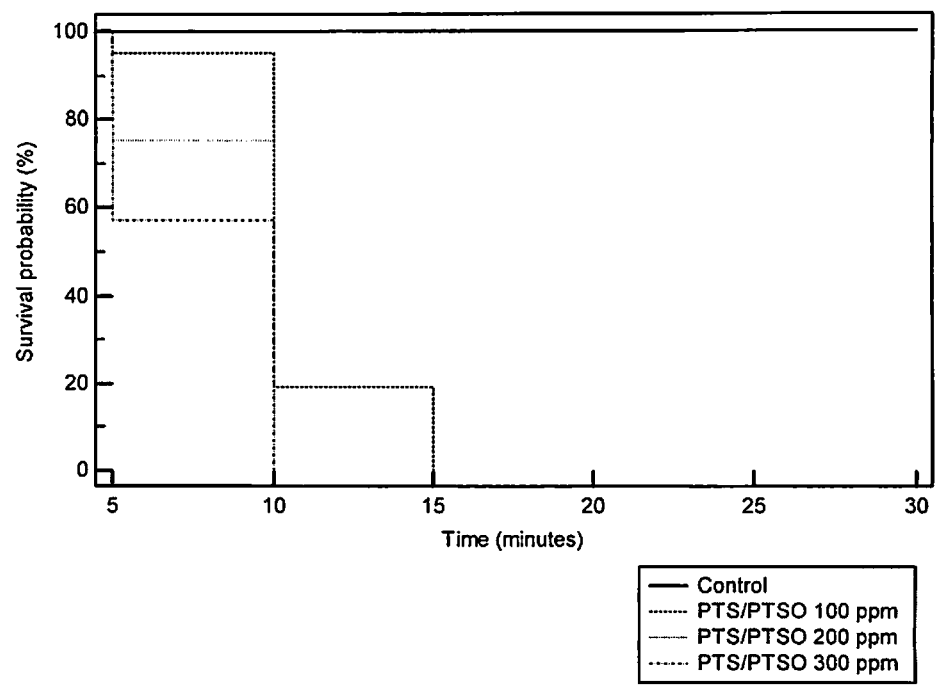
FIG. 4 illustrates the survival probability of *Caligus rogercresseyi* Nauplius I at different concentrations of PTS and PTSO.

In addition, FIG. 4 illustrates the survival probability of *Caligus rogercresseyi* Nauplius I at different concentrations of PTS and PTSO.

Figure 5:
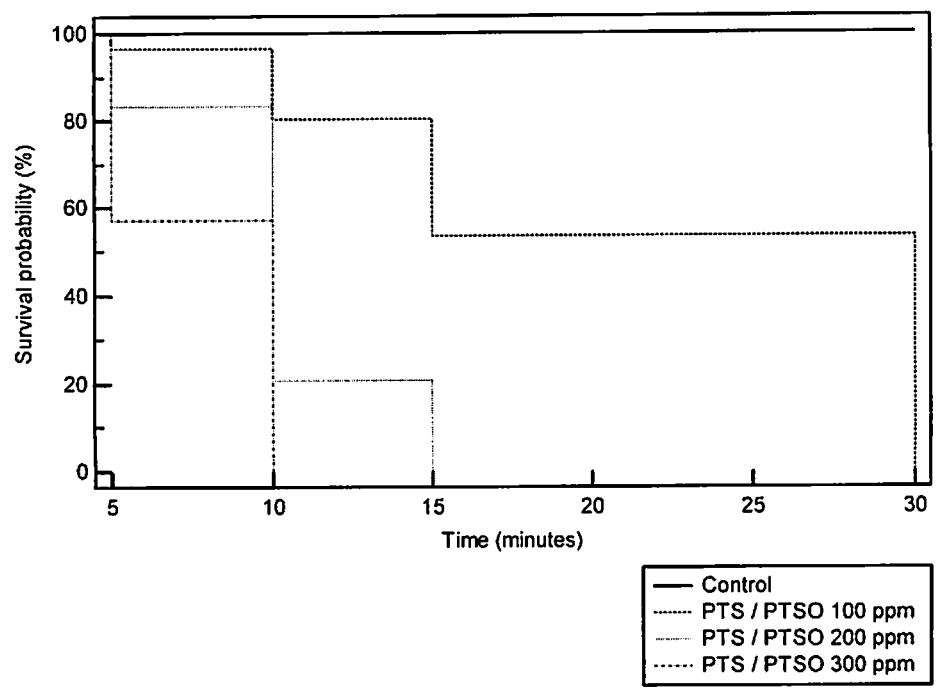
FIG. 5 illustrates the survival probability of *Caligus rogercresseyi* Nauplius II at different concentrations of PTS and PTSO.

In further illustration of the exemplary results, FIG. 5 illustrates the survival probability of *Caligus rogercresseyi* Nauplius II at different concentrations of PTS and PTSO.

Figure 6:
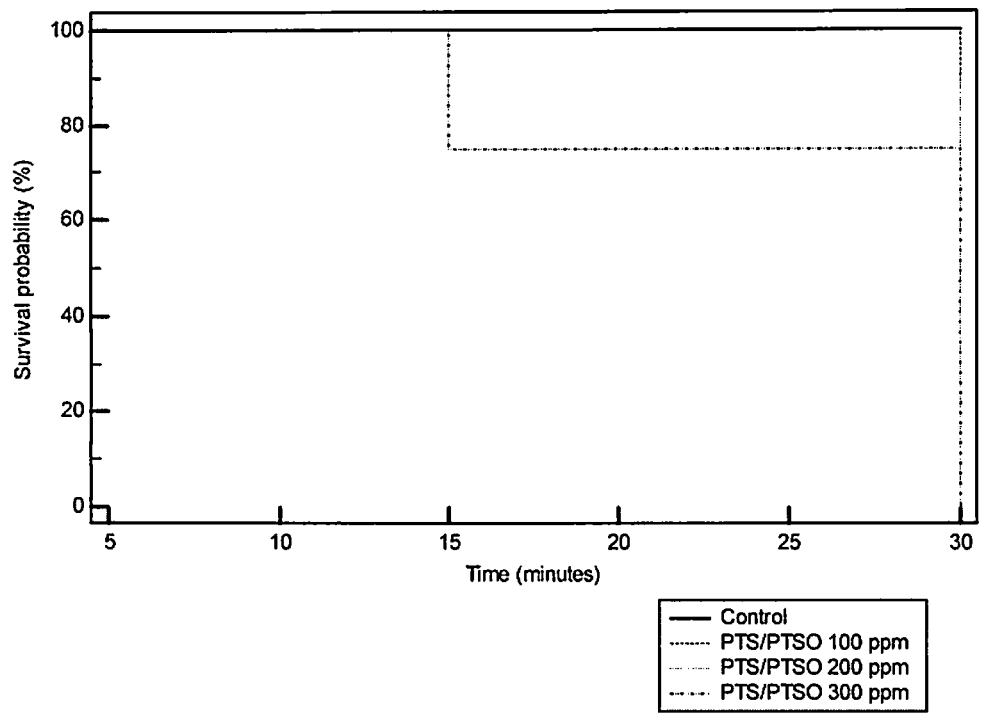
FIG. 6 illustrates the survival probability of *Caligus rogercresseyi* adults at different concentrations of PTS and PTSO.

Finally, FIG. 6 illustrates the survival probability of *Caligus rogercresseyi* adults at different concentrations of PTS and PTSO.

It is further noted that PTSO demonstrated antiparasitic activity against *Icthyobodo necator* in rainbow trout with significant reduction of infestation intensity as shown in Table 1. For each treatment and each dosage tested, infestation intensity 24 hours after the end of the assay is shown for each of the 20 fish included in each assay. Also shown is infestation intensity: high, moderate, low, minimal and zero (i.e. no *Icthyobodo necator* detected in body scrapings).

TABLE 1

| | % infestation | | | | |
| --- | --- | --- | --- | --- | --- |
| | High | Moderate | Low | minimal | zero |
| Positive control | 53 | 41 | 6 | 0 | 0 |
| PTSO (100 ppm) | 35 | 30 | 18 | 12 | 5 |
| PTSO (300 ppm) | 25 | 7 | 8 | 5 | 55 |
| Metronidazole (300 ppm) | 15 | 20 | 7 | 12 | 46 |

Of note, infestation intensity was based on a 5-point scale, as follows: Zero equals *Ichthyobodo necator* not being detected in the sample; Minimal equals only 1 individual of *I. necator* being detected in the sample; Low equals more than 1 individual of parasite being detected in the sample, the average number per microscope field being less than 10; Moderate equals an average number of individuals per microscope field of 10 to 50; High equals an average number of individuals per microscope field of more than 50.

Figure 7:
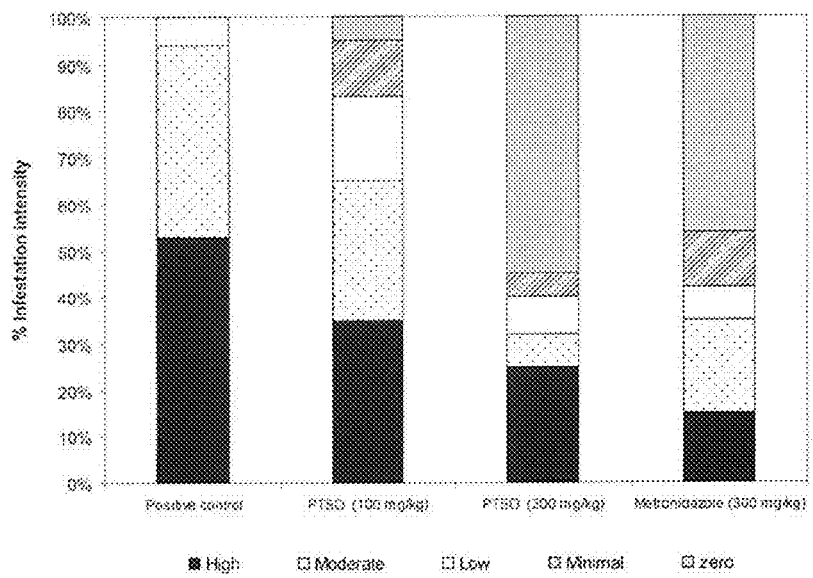
FIG. 7 illustrates assay effectiveness at different concentrations of PTSO on the control of *Icthyobodo necator* in rainbow trout.

Further, FIG. 7 illustrates assay effectiveness at different concentrations of PTSO on the control of *Icthyobodo necator* in rainbow trout.

Figure 8:
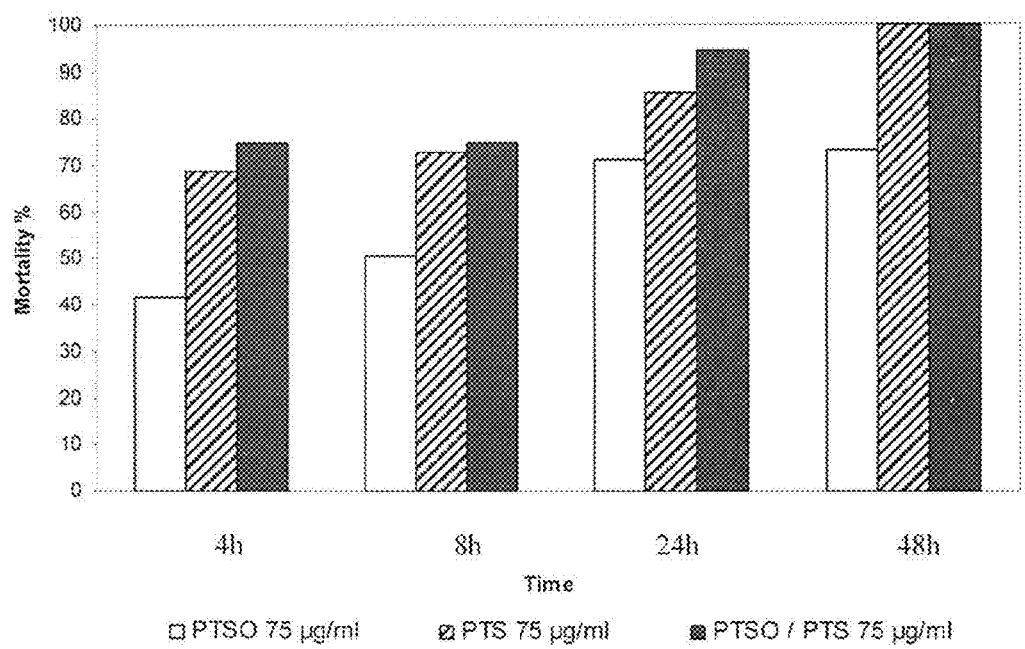
FIG. 8 illustrates in vitro activity of PTS, PTSO, and a mixture of both (1:1) against L3 larvae of *Hysterotylacium aduncum* at the concentration tested (75 ppm), where activity is expressed as mortality; and, FIG. 9 illustrates in vitro activity of PTSO against L3 larvae of *Anisakis* type I at the concentrations tested (200, 300 and 500 ppm), where activity is expressed as mortality.

In addition, PTS and PTSO demonstrated significant antiparasitic activity against L3 larvae of *Hysterotylacium aduncum* and *Anisakis* type I, as shown in FIG. 8.

Figure 9:
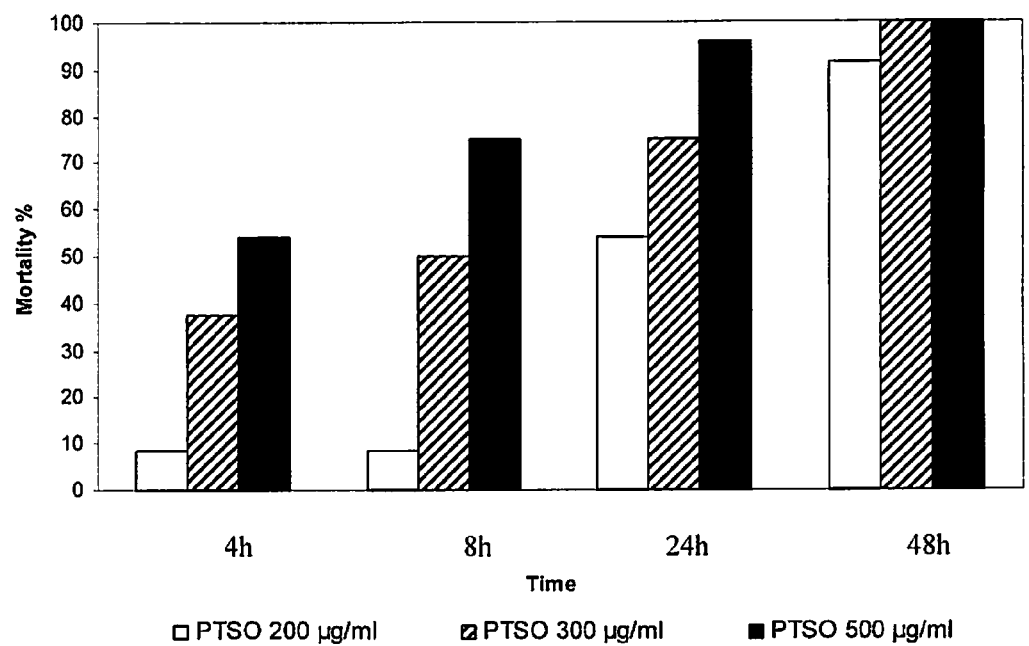

Specifically, FIG. 8 illustrates in vitro activity of PTS, PTSO, and a mixture of both (1:1) against L3 larvae of *Hysterotylacium aduncum* at the concentration tested (75 ppm), where activity is expressed as mortality. In addition, in FIG. 9, in vitro activity of PTSO against L3 larvae of *Anisakis* type I at the concentrations tested (200, 300 and 500 ppm), where activity is expressed as mortality is illustrated.

We claim:

1. A method for reducing parasites in aquatic animals, comprising:
   reducing a plurality of crustaceans infecting an aquatic animal by administrating to the aquatic animal propyl propane thiosulfinate (PTS), the PTS having a formula R—SOa-S—R, where R represents n-propyl group (—CH$_2$—CH$_2$—CH$_3$) and a is 1 and also administrating propyl propane thiosulfonate (PTSO), the PTSO having a formula R—SOa-S—R, where R represents n-propyl group (—CH$_2$—CH$_2$—CH$_3$) and a is 2, so that a combination of PTS and PTSO is administered to the aquatic animal, the concentration of PTS and PTSO is between at least one and no more than five thousand parts per million (1-5000 ppm).

2. The method of claim 1, wherein the concentration of PTSO is between at least ten and no more than four hundred parts per million (10-400 ppm).

3. The method of claim 1, wherein the concentration of PTS is between at least ten and no more than four hundred parts per million (10-400 ppm).

4. The method of claim 1, wherein the combination of PTS and PTSO is orally administered to the aquatic animal.

5. The method of claim 1, wherein the plurality of crustaceans is an aquatic parasite.

6. The method of claim 1, wherein the crustacean is a sea lice.

7. The method of claim 4, wherein the combination of PTS and PTSO is orally administered to the aquatic animal in feed.

* * * * *